United States Patent [19]
Pennig

[11] Patent Number: 5,320,623
[45] Date of Patent: Jun. 14, 1994

[54] CLAMPING COUPLING FOR AN EXTERNAL FIXATOR

[75] Inventor: Dietmar Pennig, Münster, Fed. Rep. of Germany

[73] Assignee: Orthofix S.r.l., Bussolengo, Italy

[21] Appl. No.: 914,440

[22] Filed: Jul. 15, 1992

[30] Foreign Application Priority Data

Jul. 16, 1991 [DE] Fed. Rep. of Germany ....... 4123439

[51] Int. Cl.$^5$ .............................................. A61B 17/54
[52] U.S. Cl. ...................... 606/59; 606/54; 403/83; 403/59
[58] Field of Search ................. 606/53-59, 606/61, 104, 105; 403/83, 88, 93, 110, 59, 58, 53, 379, 378

[56] References Cited

U.S. PATENT DOCUMENTS

| | | | |
|---|---|---|---|
| Re. 31,809 | 1/1985 | Danieletto et al. ............ | 606/57 |
| 1,789,060 | 1/1931 | Weisenbach ................ | 606/54 |
| 2,391,537 | 12/1945 | Anderson .................... | 606/59 |
| 4,135,505 | 1/1979 | Day ............................ | 403/110 X |
| 4,312,336 | 1/1982 | Dianeletto et al. ........... | 606/59 X |
| 4,604,997 | 8/1986 | De Bastiani et al. ......... | 606/55 |
| 4,628,919 | 12/1986 | Clyburn ...................... | 606/55 |
| 4,988,349 | 3/1991 | Pennig ........................ | 606/58 |
| 5,160,335 | 11/1992 | Canadell et al. ............. | 606/57 X |
| 5,207,676 | 5/1993 | Wagenknecht ............... | 606/59 |

OTHER PUBLICATIONS

Osteotaxis, Fixateur Extrene, Hoffmanns, Jun. 1977.
Orthofix, Dynamic Axial Fixation, 1982.

Primary Examiner—Robert A. Hafer
Assistant Examiner—Brian E. Hanlon
Attorney, Agent, or Firm—Hopgood, Calimafde, Kalil & Judlowe

[57] ABSTRACT

A clamping coupling for fixing of bone screws or pins, and connecting these bone screws or pins to an external fixator, includes an additional transverse clamping coupling to achieve better external-fixator anchorage when fractures extend up into the joint (condyle) of the femur. A selectively adjustable asymmetric arrangement permits fixed settings parallel to the longitudinal axis of the femur, while a lateral offset takes into account the natural lateral offset of the centerline of the condyle of the femur with respect to the longitudinal axis of the femur.

8 Claims, 1 Drawing Sheet

CLAMPING COUPLING FOR AN EXTERNAL FIXATOR

BACKGROUND OF THE INVENTION

The invention relates to orthopedic-fixation devices and in particular to a clamping coupling for a fixator of the nature disclosed in U.S. Pat. No. 4,312,339 (now Reissue Pat. No. Re. 31,809).

Said patent discloses an external fixator having a central body part with clamping means at each of the respective ends of the body part. Each of the clamping means is developed (1) to receive and fix in place bone screws or pins and (2) to detachably achieve a ball-joint connection to the central body part, via a bayonet lock or via a threaded lock. In this way, the bone screws are connected to the central body part of the fixator.

In fractures which extend into the end of a bone, for example, into the condyle or joint end of a femur, clamping couplings of existing construction present difficulties in respect of obtaining sufficient assurance of fixation at the condyle region.

BRIEF STATEMENT OF THE INVENTION

The object of the invention is to provide improved structure in a clamping coupling for an external fixator, whereby to achieve substantially enhanced anchorage to the condyle region of a fractured limb, particularly when the fracture extends into the joint. wherein the clamping coupling provides a first clamping component of conventional configuration for clamping a first array of bone screws, pins or the like along a first orientation axis, in conjunction with a second clamping component of similar configuration for clamping a second array of bone screws, pins or the like along a second orientation axis. The respective orientation axes are preferably orthogonally related, and the orientation axis of the second clamping component is not only selectively rotatable about the orientation axis of the first component but is also releasably clamped in any selected rotational position.

More specifically, in the preferred form to be described in detail, the first clamping component comprises first and second elongate body parts or half shells having confronting surfaces with an array of spaced parallel grooves for clamping engagement with a first pair or other plurality of bone screws, pins or the like, distributed along the first orientation axis; one longitudinal end of these body parts mounts ball-joint connection means for detachable connection to an end of an external fixator, while the opposite longitudinal end of said one body part is configured for selectively clamped rotational mounting of the second clamping component. Specifically, the second clamping component comprises third and fourth elongate body parts or half shells having confronting surfaces with an array of spaced parallel grooves for clamping engagement with another pair or other plurality of bone screws, pins or the like distributed along the second orientation axis, the rotational mounting of the second clamping component being via one of the body parts of the second clamping component. In this connection, it is considered to be essential that the rotary the axis of connection between the respective clamping components shall be at offset from the longitudinal center of the array of bone-screw grooves of the second clamping component; this offset will be understood to take into account the lateral offset (about 7-mm) between the respective centerlines of the shank and of the adjacent condyle of a femur.

DETAILED DESCRIPTION

Figure 1:
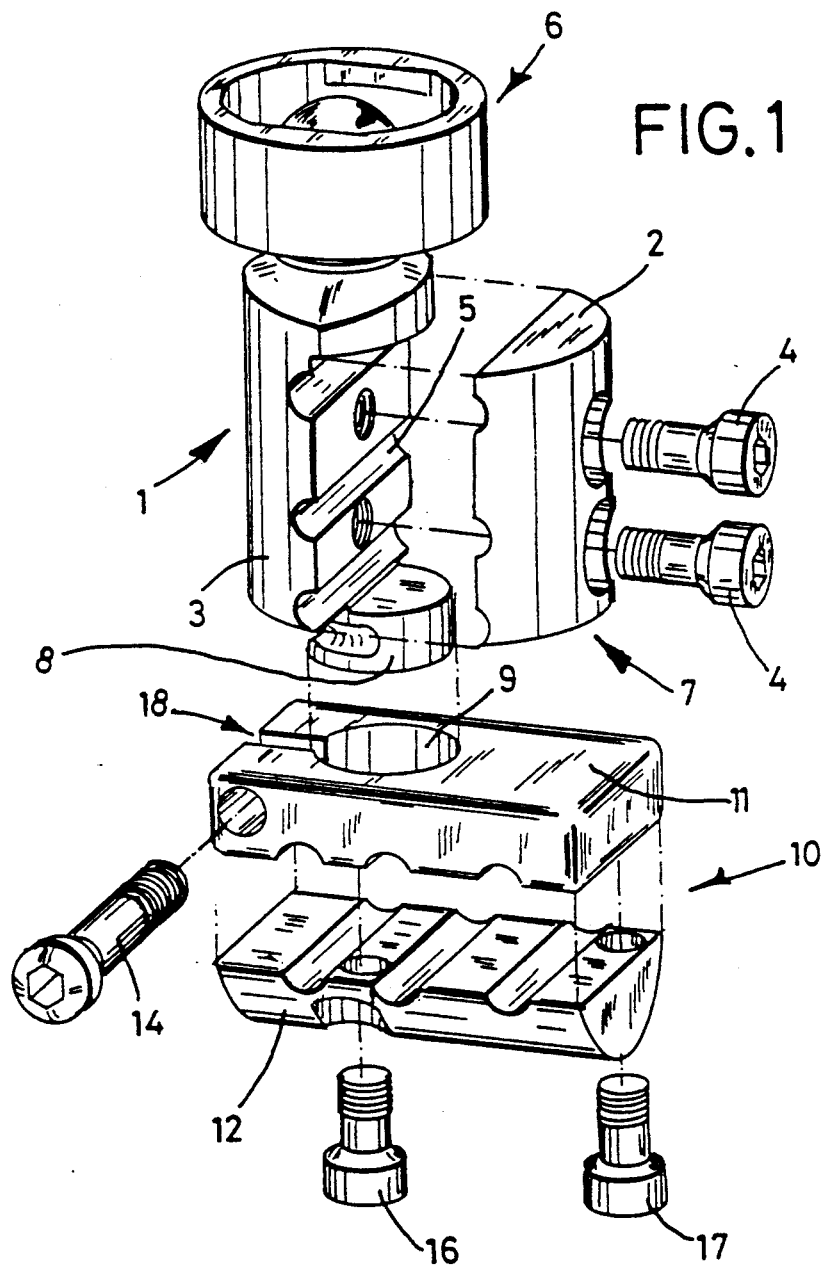
Figure 2:
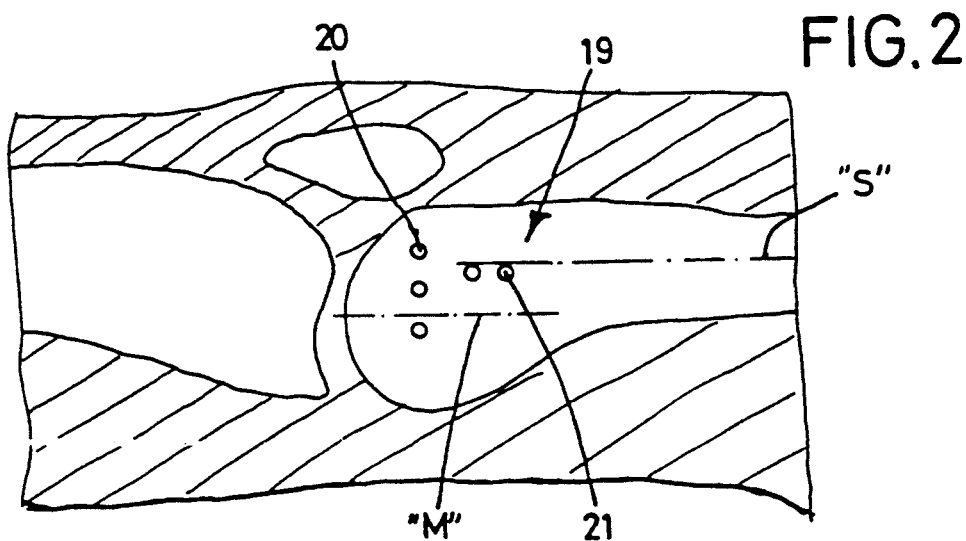

The presently preferred embodiment of the invention will be described in detail in conjunction with the accompanying drawings, in which:

FIG. 1 is an exploded perspective view of cooperating parts of the new coupling; and FIG. 2 is a purely diagrammatic view of a condyle, in illustration of the above-noted offset, with indication of the respective centerlines of the adjacent shank and condyle regions of a single bone, such as a femur.

In FIG. 1, a clamping coupling 1 has a ball-joint connection 6 for a bayonet lock and consists essentially of an elongate body comprising two half shells 2 and 3, which can be fastened on and against each other by screws 4. Confronting surfaces of the half shells 2 and 3 are provided with a longitudinal array of spaced arcuate recesses 5 into which bone screws or bone pins can be inserted, these bone screws or the like being then also held fast by clamping the half shells 2 and 3 to each other. By the means thus far described, a conventional connection is established between a bone (via bone screws or the like) to one end of a fixator proper; and the elongate body (shells 2, 3) will sometimes be referred to as the first clamping component, with the ball-joint connection 6 at one longitudinal end of this elongate body, specifically body shell 3.

In the embodiment shown, and in accordance with the invention, the opposite longitudinal end of the clamping coupling 1, namely, body shell 3, is configured for selectively fixed rotational support of a second clamping component 10 which is oriented transverse to the elongation axis of the clamping coupling 1. As with coupling 1, the second clamping component 10 consists essentially of an elongate body comprising two half shells 11 and 12, which can be fastened to and against each other by screws 16, 17; and confronting surfaces of the half shells 11, 12 are provided with a longitudinal array of spaced arcuate recesses for reception of bone screws, bone pins or the like, which can be held fast by clamping the half shells 11, 12 to each other.

In the form shown, the indicated rotary connection of the two clamping components involves a cylindrical stud formation 8 integrally formed with the body half-shell 3, and on an axis which is eccentrically offset from and parallel to the central axis of body (2, 3) and ball-joint connection 6. The stud formation 8 fits a receiving bore formation 9 in a slitted end of the body half shell 11, the slit being indicated at 18. A clamping screw 14 for control of slit width is adjustable to releasably clamp stud formation 8 in a selected angular orientation of the second clamping component 10 about the eccentrically offset axis of stud formation 8. The clamping screw 14 is seen in FIG. 1 to have a cylindrical shank which is threaded only at its distal end, and the bore in which this cylindrical shank is journalled will be understood to geometrically intersect the profile of a circumferential groove in stud formation 8, for purposes of axially retaining the clamping components, when the clamp action of screw 14 is relaxed to permit the indicated rotary adjustment.

From the drawing, it can also clearly be noted that the axis of the receiving bore 9 is offset eccentrically from the longitudinal center of the half shell 11, this eccentric offset amounting to about 7-mm. In this way, there is obtained a lateral offset between the transverse clamping coupling 10 and the clamping coupling 1 which takes into account the lateral offset of the shank center line of the femur, namely, as is clear from the showing in FIG. 2.

In FIG. 2, a condyle 19 is identified at the end of the associated shank of a femur; the shank center line is indicated at "S", while the center line of the condyle is designated "M". It is clear that these two centerlines are offset from each other and that transversely spaced holes to receive bone screws or bone pins fixed by the transverse clamping coupling 10 (astride the condyle centerline M) can be noted at 20, and longitudinally spaced holes for the bone screws or bone pins fixed by the conventional clamping coupling 10 are noted at 21. From FIG. 2, it is also clear that the indicated eccentric offset has made it possible to provide the longitudinally spaced holes 21 on or immediately adjacent the central axis S of the shank of the femur.

Expressed differently, the above-described eccentric arrangement of the connecting point, i.e., of the connecting stud 8, makes it possible to set the fastening device 1 parallel to the longitudinal axis of the bone. And it can be further observed that combined use of the described eccentric offset of the axis of stud (8) and of the off-center location of its receiving bore 9 will enable a continuously variable range of adjustment of the net offset, e.g., to best adapt the described new clamping coupling to the size variations encountered in femurs of different human beings.

I claim:

1. A clamping coupling for the fixing of spaced bone screws or bone pins in separate arrays which are orthogonally related, said coupling comprising a first elongate coupling unit having a ball-joint connection at one end for connection to an external fixator, and a second elongate coupling unit having adjustably clamped rotary connection to the other end of said first coupling unit, the elongate direction of said second coupling unit being transverse to the elongate direction of said first coupling unit, said first coupling unit having means for clamped fixation of a first plurality of bone screws or bone pins in a first longitudinally spaced array, and said second coupling unit having means for clamped fixation of a second plurality of bone screws or bone pins in longitudinally spaced array along said second coupling unit and therefore in transversely spaced array with respect to said first array.

2. The clamping coupling of claim 1, in which said first coupling unit has a central axis through the ball center of the ball joint, and in which said rotary connection is about an axis eccentric to said central axis.

3. The clamping coupling of claim 1, in which the rotary connection is about an axis which is offset from the center of said transversely spaced array.

4. The clamping coupling of claim 1, in which said first coupling unit has a central axis through the ball center of the ball joint, in which said rotary connection is about an axis eccentric to said central axis, and in which the axis of the rotary connection is offset from the center of said transversely spaced array.

5. A clamping coupling for the fixing in place of bone screws or bone pins in longitudinally spaced and in transversely spaced array and for connecting the same to an external fixator, said coupling comprising:

a first and longitudinally extending clamp unit consisting of two half shells connected and clamped together by screws, said half shells having recesses for clamped fixation of bone screws or bone pins in longitudinally spaced array, and ball-joint connecting means at one end of one of said half shells;

a second and transversely extending clamp unit consisting of two further half shells connected and clamped together by screws, said two further half shells having recesses for clamped fixation of bone screws or bone pins in transversely spaced array; and releasably securable rotary connection means coacting between the other end of said one of said half shells and one of said further half shells, said rotary connection means mounting said transversely extending clamp unit for releasably securable rotary orientation about the longitudinal axis of said longitudinally extending clamp unit.

6. The clamping coupling of claim 5, in which said releasably securable rotary connection means comprises a cylindrical stud at said other end of said one of said half shells, and in which said one of said further half shells has a receiving bore for selectively rotatable and clampable connection to said stud.

7. The clamping coupling according to claim 6, in which the central axis of said bore is at offset from the center of the transversely spaced array.

8. The clamping coupling of claim 6, in which the axis of said stud is aligned with the longitudinal axis of said longitudinally extending clamp unit and with the center of said ball-joint connecting means.

* * * * *